United States Patent
Borgmann et al.

(10) Patent No.: US 7,238,848 B2
(45) Date of Patent: *Jul. 3, 2007

(54) METHOD FOR SEPARATING DIMETHYL ETHER FROM AN OLEFIN-CONTAINING PRODUCT STREAM

(75) Inventors: Wilfried Borgmann, Baierbrunn (DE); Josef Kunkel, Bauting (DE); Helmut Fritz, Munich (DE); Gerhard Lauermann, Bad Tolz (DE); Roland Walzl, Feldafing (DE); Klaus Muller, Kirchseeon (DE)

(73) Assignee: ExxonMobil Chemical Patents Inc., Houston, TX (US)

( * ) Notice: Subject to any disclaimer, the term of this patent is extended or adjusted under 35 U.S.C. 154(b) by 515 days.

This patent is subject to a terminal disclaimer.

(21) Appl. No.: 10/292,730

(22) Filed: Nov. 12, 2002

(65) Prior Publication Data

US 2004/0064009 A1 Apr. 1, 2004

(51) Int. Cl.
*C07C 7/04* (2006.01)
*C07C 1/20* (2006.01)

(52) U.S. Cl. ....................... 585/809; 585/639
(58) Field of Classification Search ............... 585/809, 585/639

See application file for complete search history.

(56) References Cited

U.S. PATENT DOCUMENTS

| | | | |
|---|---|---|---|
| 2,456,584 A * | 12/1948 | Everett et al. | 585/408 |
| 4,474,647 A | 10/1984 | Asselineau et al. | 203/49 |
| 4,499,327 A | 2/1985 | Kaiser | 585/640 |
| 5,090,977 A | 2/1992 | Strack et al. | 62/23 |
| 5,609,734 A | 3/1997 | Streicher et al. | 203/39 |
| 5,714,662 A | 2/1998 | Vora et al. | 585/640 |
| 5,914,433 A | 6/1999 | Marker | 585/313 |
| 5,990,369 A | 11/1999 | Barger et al. | 585/640 |
| 6,049,017 A | 4/2000 | Vora et al. | 585/324 |
| 6,121,504 A | 9/2000 | Kuechler et al. | 585/640 |

* cited by examiner

*Primary Examiner*—Thuan Dinh Dang

(57) ABSTRACT

A method for processing an olefin-containing product stream that contains dimethyl ether as a by-product is described. Such a product stream arises, for example, in the synthesis of olefin from methanol. For separation of the dimethyl ether from the product stream, it is proposed that at least a partial stream chiefly containing $C_3$ hydrocarbons is separated from the product stream by fractionation, and is sent to a rectification column ($C_3$ splitter) (16) for separation of propylene and propane. The dimethyl ether goes together with the propane into the bottom of the rectification column in the rectification process and can be withdrawn (42). A substantially pure propylene product (41), which contains at most only traces of dimethyl ether, can be removed from the top of the rectification column.

3 Claims, 1 Drawing Sheet

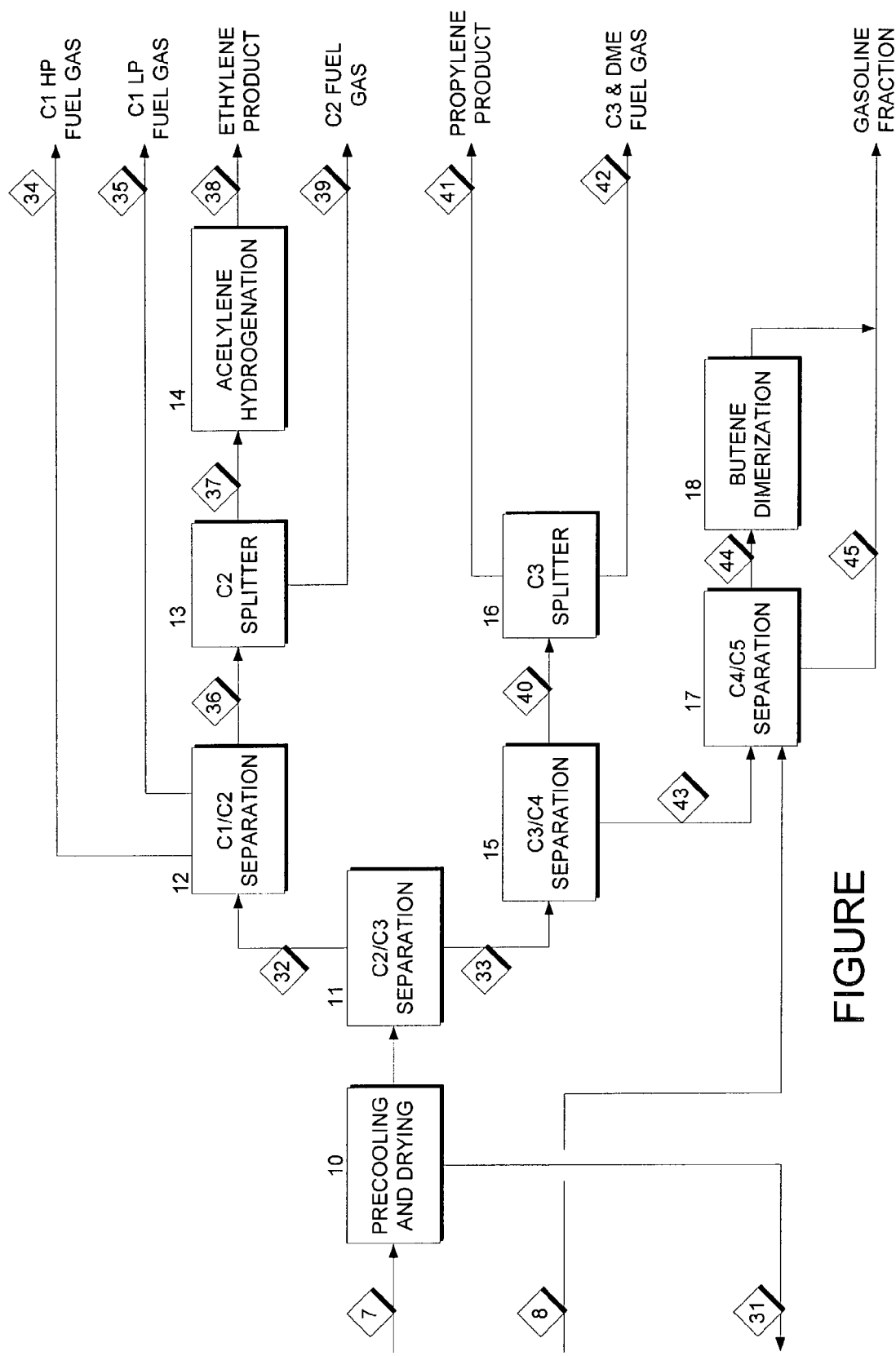
FIGURE

METHOD FOR SEPARATING DIMETHYL ETHER FROM AN OLEFIN-CONTAINING PRODUCT STREAM

This application claims benefit of the filing date of German Patent Application No. 101 50 479.9, filed Oct. 16, 2001 and the PCT Application No. PCT/US02/31046 filed Sep. 30, 2002, the contents of which are fully incorporated herein by reference.

FIELD OF THE INVENTION

The invention concerns a method for separating dimethyl ether from an olefin-containing product stream that contains dimethyl ether as by-product, where the product stream is sent to fractionation, optionally after dewatering, compression and drying.

BACKGROUND OF THE INVENTION

An interesting alternative to olefin production from petroleum is olefin synthesis from methanol. Methanol is considered to be a readily storable and manageable intermediate product for utilization of hitherto unused natural gas. Thus, the increasing demand for olefin could also be served through the use of very cheap methane. For this reason, processes are being developed that obtain short-chain olefins from methanol. Such processes operate, for example, catalytically according to the overall equation $2CH_3OH \rightarrow C_2H_4 + 2H_2O$. Besides the desired olefins, ethylene and propylene, undesired by-products also arise in the catalytic process. One undesired by-product is dimethyl ether. The problem of removing dimethyl ether from the product stream has not been satisfactorily solved up to now. Special absorber materials that are supposed to remove the dimethyl ether from the product stream have already been considered. However, it is difficult to find a suitable absorber or adsorber material for this purpose.

SUMMARY OF THE INVENTION

This invention provides a method of separating dimethyl ether from an olefin stream synthesized from methanol or other oxygenate. The dimethyl ether is separated from the olefin product stream in a novel, yet economical, way. In one embodiment, the invention provides a method for removing dimethyl ether from an olefin-containing stream. The method includes fractionating an olefin-containing stream, which comprises a $C_3$ hydrocarbon stream and dimethyl ether, to separate the $C_3$ hydrocarbon stream along with the dimethyl ether from the olefin-containing stream. The $C_3$ hydrocarbon stream containing the dimethyl ether is then sent to a rectification column. Propylene is removed from a top portion of the rectification column, and propane is removed from a bottom portion of the rectification column. The dimethyl ether is also removed from the bottom portion of the rectification column along with the propane.

In another embodiment of the invention, the propylene removed from the top portion of the rectification column is substantially free of dimethyl ether. Preferably, the propylene removed from the top portion of the rectification column contains less than 6 ppm by weight dimethyl ether. More preferably, the propylene removed from the top portion of the rectification column contains less than 3 ppm by weight dimethyl ether.

BRIEF DESCRIPTION OF THE DRAWINGS

The attached FIGURE shows an example of but one type of flow scheme of the invention in which propane ($C_3$) and dimethyl ether (DME) are separated from a propylene-containing stream to provide a propylene product stream that contains at most only traces of DME.

DETAILED DESCRIPTION OF THE INVENTION

The problem of removing dimethyl ether from an olefin stream is solved in accordance with the invention by separating at least a partial stream largely containing $C_3$ hydrocarbons from an olefin product stream by fractionation. The separated stream containing the $C_3$ hydrocarbons is sent to a rectification column ($C_3$ splitter) for separation of propylene and propane. A propylene product stream is taken from the top of this rectification column; and propane, and possibly other $C_3$ hydrocarbons, as well as dimethyl ether, are removed from the bottom portion of the rectification column so that a propylene product stream containing at most only traces of dimethyl ether is obtained.

The invention is based on fractionating the olefin stream so that dimethyl ether follows with the $C_3$ hydrocarbons in the separation process. Thus, dimethyl ether is sent with propylene, propane, and possibly other $C_3$ hydrocarbons, to a $C_3$ splitter or rectification column in the fractionation process. Surprisingly, it has now been found that the dimethyl ether goes nearly completely into the bottom portion of the rectification column along with the propane. The propylene is taken from the top portion of the column, and is substantially free of dimethyl ether. The purity of the propylene product stream is at least high enough such that less than about 6 ppm by weight, preferably less than about 3 ppm by weight, dimethyl ether remain in the propylene product stream.

Accordingly, the invention offers the advantage that no additional devices are needed for separating the dimethyl ether from the propylene product stream. The $C_3$ splitter that would be conventionally used to separate propane from the propylene can also be used to separate the undesirable dimethyl ether from the propylene.

In one embodiment of the invention, the olefin stream containing the dimethyl ether is obtained by contacting methanol with a molecular sieve catalyst. Although the use of methanol to produce the olefin stream is preferred, other oxygenate components can be used as a feed. Such oxygenates comprise at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol includes an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Dimethyl ether, or a mixture of dimethyl ether and methanol, are also preferred feeds.

Molecular sieves capable of converting an oxygenate such as methanol to an olefin compound include zeolites as well as non-zeolites, and are of the large, medium or small pore type. Small pore molecular sieves are preferred in one embodiment of this invention, however. As defined herein, small pore molecular sieves have a pore size of less than about 5.0 angstroms. Generally, suitable catalysts have a pore size ranging from about 3.5 to about 5.0 angstroms, preferably from about 4.0 to about 5.0 angstroms, and most preferably from about 4.3 to about 5.0 angstroms.

Zeolite materials, both natural and synthetic, have been demonstrated to have catalytic properties for various types of hydrocarbon conversion processes. In addition, zeolite materials have been used as adsorbents, catalyst carriers for various types of hydrocarbon conversion processes, and other applications. Zeolites are complex crystalline aluminosilicates which form a network of $AlO_2^-$ and $SiO_2$ tetrahedra linked by shared oxygen atoms. The negativity of the tetrahedra is balanced by the inclusion of cations such as alkali or alkaline earth metal ions. In the manufacture of some zeolites, non-metallic cations, such as tetramethylammonium (TMA) or tetrapropylammonium (TPA), are present during synthesis. The interstitial spaces or channels formed by the crystalline network enable zeolites to be used as molecular sieves in separation processes, as catalyst for chemical reactions, and as catalyst carriers in a wide variety of hydrocarbon conversion processes.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof, but also materials which contain suitable replacement atoms for such silicon and aluminum atoms.

One type of olefin forming catalyst capable of producing large quantities of ethylene and propylene is a silicoaluminophosphate (SAPO) molecular sieve. Silicoaluminophosphate molecular sieves are generally classified as being microporous materials having 8, 10, or 12 membered ring structures. These ring structures can have an average pore size ranging from about 3.5 to about 15 angstroms. Preferred are the small pore SAPO molecular sieves having an average pore size of less than about 5 angstroms, preferably an average pore size ranging from about 3.5 to about 5 angstroms, more preferably from about 3.5 to about 4.2 angstroms. These pore sizes are typical of molecular sieves having 8 membered rings.

According to one embodiment, substituted SAPOs can also be used in oxygenate to olefin reaction processes. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [$MeO_2$] tetrahedral unit. The [$MeO_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an $AlPO_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of $MO_2$, $AlO_2$ and $PO_2$ tetrahedral units. These as manufactured structures (which contain template prior to calcination) can be represented by empirical chemical composition, on an anhydrous basis, as:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the *Atlas of Zeolite Structural Types,* W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition, according to an embodiment, preferably comprises from about 1% to about 99%, more preferably from about 5% to about 90%, and most preferably from about 10% to about 80%, by weight of molecular sieve. It is also preferred that the catalyst composition have a particle size of from about 20 angstroms to about 3,000 angstroms, more preferably from about 30 angstroms to about 200 angstroms, most preferably from about 50 angstroms to about 150 angstroms.

The catalyst can be subjected to a variety of treatments to achieve the desired physical and chemical characteristics. Such treatments include, but are not necessarily limited to, hydrothermal treatment, calcination, acid treatment, base treatment, milling, ball milling, grinding, spray drying, and combinations thereof.

A molecular sieve catalyst particularly useful in making ethylene and propylene is a catalyst which contains a combination of SAPO-34, and SAPO-18 or ALPO-18 molecular sieve. In a particular embodiment, the molecular sieve is a crystalline intergrowth of SAPO-34, and SAPO-18 or ALPO-18.

To convert methanol or other oxygenate to olefin, conventional reactor systems can be used, including fixed bed, fluid bed or moving bed systems. Preferred reactors of one embodiment are co-current riser reactors and short contact time, countercurrent free-fall reactors. Desirably, the reactor is one in which an oxygenate feedstock can be contacted with a molecular sieve catalyst at a weight hourly space velocity (WHSV) of at least about 1 $hr^{-1}$, preferably in the range of from about 1 $hr^{-1}$ to 1000 $hr^{-1}$, more preferably in the range of from about 20 $hr^{-1}$ to about 1000 $hr^{-1}$, and most preferably in the range of from about 50 $hr^{-1}$ to about 500 $hr^{-1}$. WHSV is defined herein as the weight of oxygenate, and reactive hydrocarbon which may optionally be in the feed, per hour per weight of the molecular sieve in the reactor. Because the catalyst or the feedstock may contain other materials which act as inerts or diluents, the WHSV is calculated on the weight basis of the oxygenate feed, and any reactive hydrocarbon which may be present with the oxygenate feed, and the molecular sieve contained in the reactor.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow with a relatively high content of oxygenated olefin by-products being found in the olefin product. However, the selectivity to ethylene and propylene at reduced temperatures may be increased. At the upper end of the temperature range, the process may not form an optimum amount of ethylene and propylene product, but the conversion of oxygenate feed will generally be high.

Operating pressure also may vary over a wide range, including autogenous pressures. Effective pressures include, but are not necessarily limited to, a total pressure of at least 1 psia (7 kPa), preferably at least about 5 psia (34 kPa). The process is particularly effective at higher total pressures, including a total pressure of at least about 20 psia (138 kPa). Preferably, the total pressure is at least about 25 psia (172 kPa), more preferably at least about 30 psia (207 kPa). For practical design purposes it is desirable to use methanol as the primary oxygenate feed component, and operate the reactor at a pressure of not greater than about 500 psia (3445 kPa), preferably not greater than about 400 psia (2756 kPa), most preferably not greater than about 300 psia (2067 kPa).

Undesirable by-products can be avoided by operating at an appropriate gas superficial velocity. As the gas superficial velocity increases the conversion decreases avoiding undesirable by-products. As used herein, the term, "gas superficial velocity" is defined as the combined volumetric flow rate of vaporized feedstock, which includes diluent when present in the feedstock, as well as conversion products, divided by the cross-sectional area of the reaction zone.

Because the oxygenate is converted to a product having significant quantities of ethylene and propylene while flowing through the reaction zone, the gas superficial velocity may vary at different locations within the reaction zone. The degree of variation depends on the total number of moles of gas present and the cross section of a particular location in the reaction zone, temperature, pressure and other relevant reaction parameters.

In one embodiment, the gas superficial velocity is maintained at a rate of greater than 1 meter per second (m/s) at least one point in the reaction zone. In another embodiment, it is desirable that the gas superficial velocity is greater than about 2 m/s at least one point in the reaction zone. More desirably, the gas superficial velocity is greater than about 2.5 m/s at least one point in the reaction zone. Even more desirably, the gas superficial velocity is greater than about 4 m/s at least one point in the reaction zone. Most desirably, the gas superficial velocity is greater than about 8 m/s at least one point in the reaction zone.

According to yet another embodiment of the invention, the gas superficial velocity is maintained relatively constant in the reaction zone such that the gas superficial velocity is maintained at a rate greater than 1 m/s at all points in the reaction zone. It is also desirable that the gas superficial velocity be greater than about 2 m/s at all points in the reaction zone. More desirably, the gas superficial velocity is greater than about 2.5 m/s at all points in the reaction zone. Even more desirably, the gas superficial velocity is greater than about 4 m/s at all points in the reaction zone. Most desirably, the gas superficial velocity is greater than about 8 m/s at all points in the reaction zone.

The amount of ethylene and propylene produced in the oxygenate to olefin process can be increased by reducing the conversion of the oxygenates in the oxygenate to olefins reaction. However, reducing the conversion of feed oxygenates in the oxygenate conversion reaction tends to increase the amount of oxygenated hydrocarbons, particularly including dimethyl ether, that are present in the olefin product. Thus, control of the conversion of feed to the oxygenate reaction process can be important.

According to one embodiment, the conversion of the primary oxygenate, e.g., methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt; preferably from 98.2 wt % to 99 wt %.

In this invention, weight percent conversion is calculated on a water free basis unless otherwise specified. Weight percent conversion on a water free basis is calculated as: 100×(weight oxygenate fed on a water free basis weight—oxygenated hydrocarbon in the product on a water free basis). The water free basis of oxygenate is calculated by subtracting out the water portion of the oxygenate in the feed and product, and excluding water formed in the product. For example, the weight flow rate of methanol on an oxygenate free basis is calculated by multiplying the weight flow rate of methanol by 14/32 to remove the water component of the methanol. As another example, the rate flow rate of dimethyl ether on an oxygenate free basis is calculated by multiplying the weight flow rate of diemethylether by 40/46 to remove the water component of the dimethyl ether. If there is a mixture of oxygenates in the feed or product, trace oxygenates are not included. When methanol and/or dimethyl ether is used as the feed, only methanol and dimethyl ether are used to calculate conversion on a water free basis.

In this invention, selectivity is also calculated on a water free basis unless otherwise specified. Selectivity is calculated as: 100×wt % component/(100–wt % water–wt % methanol–wt % dimethyl ether) when methanol and/or dimethyl ether is used as the feed.

An example of the invention is shown in the FIGURE. According to the FIGURE, an olefin-containing product stream from a reactor for olefin synthesis from methanol (not shown in the FIGURE) is sent via pipe (7) to a precooling and drying step (10). Accumulated condensate (predominantly water) is removed through pipe (31). The precooled and dried product stream is then sent to a $C_2/C_3$ separation step (11). $C_1/C_2$ hydrocarbons are separated and sent through a pipe (32) to a $C_1/C_2$ separation step (12). The separated $C_1$ hydrocarbons are recovered as a high pressure (HP) and low pressure (LP) fuel gas through pipes (34) and (35). The separated $C_2$ hydrocarbons are sent through a pipe (36) to a $C_2$ splitter (13).

In the $C_2$ splitter, ethylene is separated from ethane and removed through a pipe (37). The ethylene, which can contain some acetylene, is sent to an acetylene hydrogenation step (14) and recovered as ethylene product through a pipe (39). $C_2$ combustion gas (predominantly propane) is withdrawn from the $C_2$ splitter and sent through a pipe (39).

The $C_3+$ hydrocarbons (i.e., hydrocarbons that have a boiling point greater than or equal to propylene) that are separated from the olefin stream in the $C_2/C_3$ separation step (11) are sent through pipe (33) to a $C_3/C_4$ separation step (15), where separation of the $C_3$ hydrocarbons from the heavier hydrocarbons (i.e., $C_4+$ hydrocarbons) takes place. The heavier $C_4+$ hydrocarbons are sent through a pipe (43) to a $C_4/C_5$ separation step (17). The $C_5+$ hydrocarbons are separated from the $C_4$ hydrocarbons, and ultimately sent through a line (45) for use as a gasoline fraction. The $C_4$ hydrocarbons are separated and sent through a line (44) to a butene dimerization step (18) to form dimerized hydrocarbons. The dimerized hydrocarbons are also ultimately sent through the line (45) for use as a gasoline fraction.

The $C_3$ hydrocarbons that are separated at the $C_3/C_4$ separation step (15), are sent through a pipe (40) to a $C_3$ splitter (16). Dimethyl ether, which is present in the olefin stream, also goes to the $C_3$ splitter along with the $C_3$ hydrocarbons, since it behaves like propane in the preceding fractionation steps. In the $C_3$ splitter (16), the dimethyl ether, together with the propane, goes to the bottom of the splitter, and both are removed through a pipe (42). Substantially pure propylene product, e.g., containing less than 3 ppm dimethyl ether, is obtained from the top of the $C_3$ splitter (16) through a pipe (41).

Having now fully described this invention, it will be appreciated by those skilled in the art that the invention can be performed within a wide range of parameters within what is claimed, without departing from the spirit and scope of the invention.

The invention claimed is:

1. A method for removing dimethyl ether together with propane from an olefin-containing stream synthesized from methanol, comprising:
  contacting methanol with a small pore molecular sieve catalyst to produce the olefin-containing stream;
  separating $C_1/C_2$ hydrocarbons from $C_3+$ hydrocarbons in the olefin-containing stream;

separating $C_3$ hydrocarbons along with the dimethyl ether from $C_4+$ hydrocarbons;

sending the $C_3$ hydrocarbons containing the dimethyl ether to a $C_3$ splitter, comprising a first portion on top half of the $C_3$ splitter and a second portion on the bottom half of the $C_3$ splitter;

removing propylene from the first portion of the $C_3$ splitter so that a propylene product stream containing at most only traces of dimethyl ether is obtained; and removing propane from the second portion of the $C_3$ splitter, wherein the dimethyl ether together with the propane is removed from the second portion of the $C_3$ splitter as one stream.

2. The method of claim 1, wherein the propylene removed from the first portion of the $C_3$ splitter contains less than 6 ppm by weight dimethyl ether.

3. The method of claim 2, wherein the propylene removed from the first portion of the $C_3$ splitter contains less than 3 ppm by weight dimethyl ether.

* * * * *